United States Patent
Freyer et al.

(10) Patent No.: US 6,847,033 B2
(45) Date of Patent: Jan. 25, 2005

(54) METHOD AND DEVICE FOR QUICKLY AND CONTINUALLY DETECTING CHANGES IN THE CONCENTRATION OF RADON GAS THAT IS DISSOLVED IN WATER

(75) Inventors: Klaus Freyer, Holzhausen (DE); Hanns-Christian Treutler, Naunhof (DE); Günther Just, Grosspösna (DE)

(73) Assignee: UFZ Umweltforschungszentrum Leipzing-Halle GmbH, Leipzing (DE)

(*) Notice: Subject to any disclaimer, the term of this patent is extended or adjusted under 35 U.S.C. 154(b) by 123 days.

(21) Appl. No.: 10/009,451

(22) PCT Filed: Mar. 7, 2001

(86) PCT No.: PCT/EP01/02566
§ 371 (c)(1),
(2), (4) Date: Apr. 29, 2002

(87) PCT Pub. No.: WO01/66227
PCT Pub. Date: Sep. 13, 2001

(65) Prior Publication Data
US 2002/0148958 A1 Oct. 17, 2002

Related U.S. Application Data

(63) Continuation-in-part of application No. 09/180,706, filed on Nov. 13, 1998, now Pat. No. 6,232,598.

(30) Foreign Application Priority Data
Mar. 8, 2000 (DE) .......................... 100 10 558

(51) Int. Cl.$^7$ ............................. G01N 1/14; G01N 33/18
(52) U.S. Cl. ........................ 250/255; 250/304; 250/435
(58) Field of Search ............................ 250/255, 304, 250/435, 437

(56) References Cited

U.S. PATENT DOCUMENTS

| 4,225,314 A | * | 9/1980 | Macourt ...................... 436/26 |
| 4,868,546 A | * | 9/1989 | Dumbeck ................... 340/632 |
| 5,055,674 A | * | 10/1991 | Kotrappa .................... 250/255 |
| 5,100,555 A | * | 3/1992 | Matson ......................... 95/44 |
| 5,194,158 A | * | 3/1993 | Matson .......................... 95/46 |
| 6,251,167 B1 | * | 6/2001 | Berson ........................ 95/263 |

FOREIGN PATENT DOCUMENTS

WO   WO 97/43637   11/1997   .......... G01N/33/18

OTHER PUBLICATIONS

H. Surbeck: A Radon–in–Water Monitor Based on Fast Gas Transfer Membranes, Int. Conf. Technologically Enhanced Natural Radioactivity (TENR) Caused by Non–Uranium Mining, Oct. 16–19, 1996, Szczyrk, Poland.

* cited by examiner

Primary Examiner—Albert Gagliardi
(74) Attorney, Agent, or Firm—Norris, McLaughlin & Marcus, P.A.

(57) ABSTRACT

The invention describes a method and a device for the continual and, in particular, for a fast detection of changes of the concentration of radon gas dissolved in water by means of a transfer into a measuring gas (Rn-222), which can be adopted for a variety of monitoring, control and regulation assignments.

The invention is based on the fact that a membrane, which is permeable for the radioactive noble gas radon but extensively non-permeable for water, is circum-flushed on the one side of radon-containing water and on the other side of the carrier gas with, in each case, optimised flow velocities either in parallel or in counter-flow When stable peripheral conditions are ensured, the concentration of radon in the measuring gas is directly proportional to the concentration of radon in the water.

9 Claims, 2 Drawing Sheets

METHOD AND DEVICE FOR QUICKLY AND CONTINUALLY DETECTING CHANGES IN THE CONCENTRATION OF RADON GAS THAT IS DISSOLVED IN WATER

RELATED APPLICATIONS

This application is continuation-in-part application of Ser. No. 09/180,706 filed on Nov. 13, 1998 now U.S. Pat. No. 6,232,598 issued May 15, 2001.

BACKGROUND OF THE INVENTION

The invention concerns a method for the continual and, in particular, the fast detection of changes of the concentration of radon gas dissolved in water by means of transfer into a measuring gas (Rn-222) which can be adopted for a diversity of monitoring, control and regulation assignments.

It concerns also a special device for the fast and continual transfer of radon gas (Rn-222) into a measuring gas and its further conveyance into detection systems for radon gas (Rn222) which are specially made for this purpose and which are commercially available.

The natural radioactive noble gas radon (Rn-222) occurs everywhere and constantly new, if and when the radium-226, formed in the decay series of uranium-238, decays. All geological materials contain uranium more or less. For this reason, radon is also omnipresent and can also be found in water in various concentrations. For the measurement-technical detection of the concentration of radon in water, there are numerous methods available with regard to the working principle which can be applied both in the field as well as in the laboratory.

The continual detection of concentrations of changes of radon occurring in water is of major interest for numerous and possible applications. However, the time-related dissolutions realised with various methods up to now have proven to be inadequate and/or unsuitable, so that the desired information was either non-available or only insufficiently available.

A representative selection of examples for the possible use are the optimisation of sample extraction from ground water measuring locations, the monitoring of radon carriage in spring water as one of several factors for earthquake research and, furthermore, the inspection of baineological applications of radon in water (quality assurance).

DESCRIPTION OF THE RELATED ART

The continual measurement of the concentration of radon (Rn-222) in water is known, by means of the transfer of the radon from the water through a water-tight, gas-permeable membrane, e.g., in the form of a hose, into a gas cycle (e.g., air) which is conducted through a radon measuring equipment unit, where the radon concentration in the gas cycle is determined by the measurement of the activity of the radon and its sequence products. (H. Surbeck, A Radon-in Water Monitor Based on Fast Gas Transfer Membranes, Int. Conf. Technologically Enhanced Natural Radioactivity (TENR) Caused by Non-Uranium Mining, Oct. 16–19, 1996, Szczyrk, Poland). In the closed gas cycle, and with a time-lag corresponding to the half life periods of the sequence products, an activity concentration proportional to the radon concentration in the water builds itself up.

The drawback with this device is the fact that, as a result of this time-related delay of the activity build-up, a continual determination of the radon concentration in the water, particularly a change in concentration, is only possible with a time-related dissolution of more than 15 min.

Furthermore, the WO 97/43637 describes a method and devices for the characterisation of ground water measuring locations by means of a differentiation of ground water and stand water and serves, for example, for the determination of the pump-down times, which are optimal for quality examination purposes, of ground water measuring locations as well as the recognition and localisation of defects at ground water measuring locations. The invention is based on the measurement of radon activity concentration and/or the comprehensive activity concentration of the ground water samples.

The measurement of the concentrations allows the determination of the relationship of ground water to stand water in a ground water measuring location.

A new type of flow measuring cell as well as a bore-hole probe are described.

With all known methods and devices, the measuring gas is circulated through the diffusion hose and the measuring chamber. In this way, and corresponding to the half life period of the radon-222 of 3.8 days, a concentration equilibrium slowly builds up between the surrounding water and the measuring gas. The relatively long half life period prevents the registration of fast (in the minute range) changes of the radon concentration in the water.

SUMMARY OF THE INVENTION

The invention is based on the task assignment of stating a method and a device for the fast and continual detection of changes in the concentration of radon gas dissolved in water which represent an economical and technically less sophisticated solution and which allow, either in a mobile or stationary mode, the detection of fast changes in the concentration of radon in the water with the highest possible time-related dissolution.

Accordingly, the invention provides a method for continuous and fast detection of changes in the concentration of radon gas dissolved in water, using water-tight and gas-permeable membranes. This is accomplished wherein, without the realization of a cycle, constantly new, radon-free gas is pumped through a gas zone surrounded by water and separated by a water-tight, gas-permeable membrane into a radon measuring equipment unit where it is continually measured. The radon-free gas contemplated may be air. Also, the gas, after it leaves the radon measuring equipment unit, is discharged to en ambient surrounding. The water and the measuring gas may be conducted in a counter-current along the membrane. The water and the measuring gas may be conducted parallel to the membrane. As a gas zone, a diffusion hose may be utilized.

The invention also provides a device for the continual and fast detection of the changes of concentration of radon gas which is dissolved in water. For this end, a gas zone having an inlet and an outlet is provided and is arranged in flowing water. The inlet of the gas zone is connected to a gas source and the outlet of the gas zone is connected with the inlet of a radon measuring equipment unit.

A particular advantage of the invention lies in the fact that, in all the known solutions, the existing enormous time-related delay in the detection of concentration changes of the radon gas dissolved in water is prevented and/or minimised by the fact that the gas cycle is opened.

As a difference to the known methods and devices where a defined volume of water surrounds the diffusion hose in a more or less stationary manner, radon-free measuring gas according to the invention is constantly supplied to the one side of the diffusion hose. The measuring gas takes up the radioactive noble gas radon, which diffuses through the diffusion hose from the constantly and newly supplied water parallel or in the counter-current to the measuring gas on the other side of the diffusion hose with a optimised flow velocity, and conducts it to a suitable measuring facility.

When stable peripheral conditions are ensured, the concentration of radon in the measuring gas is directly proportional to the concentration of radon in the water.

With the use of particularly suitable measuring facilities, even with small activity concentrations of a few Becquerel radon in a liter of water, time-related dissolutions in the range of approx. 2 minutes and less can be obtained.

The dimensioning and the geometric form of the membrane as well as the flow velocities required for the water and the carrier gas can be optimised as required corresponding to the concrete existing task assignments, the concentration range to be monitored and the desired time-related dissolution.

As a result of the fact that constantly new and radon-free gas, e.g., air, is pumped through the gas zone (e.g., the diffusion hose) surrounded by water, and into the radon measuring equipment unit where it is continually measured and subsequently discharged to the ambient surroundings, the build-up of sequence nuclides of the radon in the measuring gas over a longer period is avoided, thus preventing a delay of the time-related measuring effect.

For the first time, and by means of this method, it is also possible to directly detect the decline of the radon concentration.

BRIEF DESCRIPTION OF THE DRAWINGS

The invention will be better understood by the following preferred embodiments.

DETAILED DESCRIPTION OF THE PRESENTLY PREFERRED EMBODIMENTS

Figure 1:
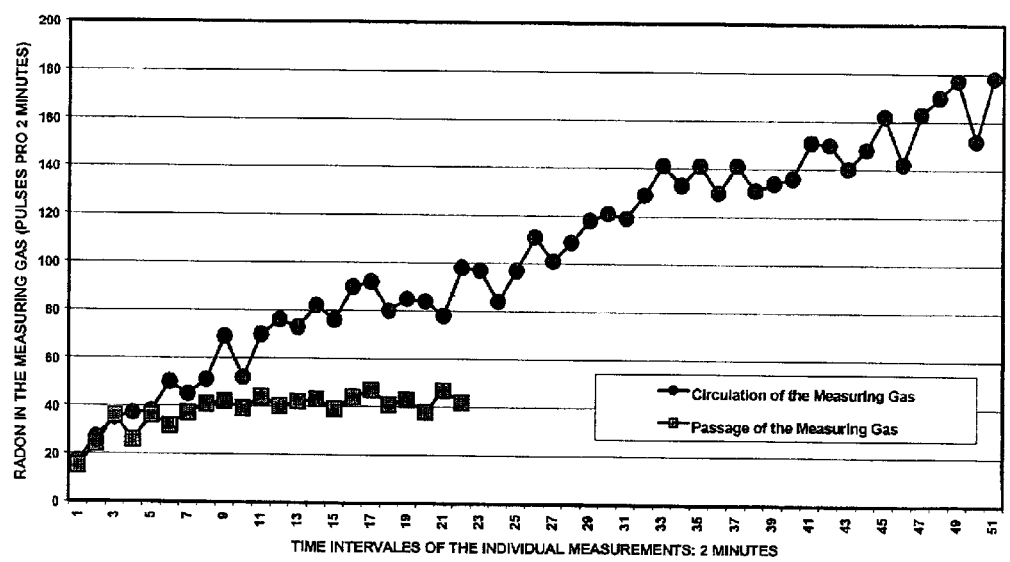
FIG. 1: This figure shows a diagram for comparison purposes between the cycle and passage flow of the measuring gas, throughput of approx. 12 liters of pipe water per minute through the probe (specific activity: approx. 1 Bq radon per liter of water).

If, as shown in FIG. 1, a measuring gas is transported in the cycle (dots), as was the case in the formerly applied measuring methods, the measuring line is then considerably contaminated and is no longer in the position to be able to detect minor activity differences with the desired time dissolution. The status of equilibrium is achieved only after approx. 2 hours.

If new measuring gas is constantly applied in the throughput mode (squares), then a constant measuring signal builds up after a few minutes which is extensively proportional to the specific activity of radon in the water, reacts quickly to sporadic activity changes and only requires minor corrections.

Figure 2:
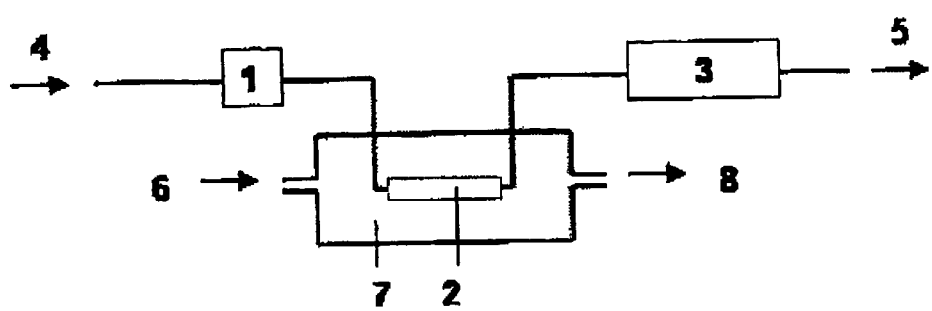

In FIG. 2 a schematic diagram shows the gas input line 4 connected to a pump 1 which is connected on the output side to a gas zone (volume) 2 located in a water container 7 which has a water input/output 6 and a water output/input 8. The gas from 2 reaches the Rn measurement equipment 3 before it exit, at gas output 5. This arrangement provides for the continual and fast detection of the changes of concentration of radon gas which is dissolved in water. For this end, a gas zone 2 has an inlet and an outlet and is arranged in flowing water 7. The inlet of the gas zone is connected to a gas source via the gas pump 1 and the outlet of the gas zone is connected with the inlet of the radon measuring equipment unit 3.

The invention is not limited to the embodiments described here. Moreover, it is possible to realise further embodiment variants by means of combination of the means and features stated above, without departing from the framework of the invention.

What is claimed is:

1. A method for continual detection of changes in concentration of radon gas dissolved in water, comprising the steps of:

continuously pumping a continuous flow of radon-free gas through a zone including water-tight and a gas-permeable membrane and being surrounded by water;

providing a radon measuring equipment unit for receiving the radon-free gas coming from the zone and from which the radon-free gas exits;

continually measuring the changes in the concentration of the radon-free gas.

2. The method according to claim 1, wherein the radon-free gas is air.

3. The method according to claim 1, further providing the step of discharging the gas, after departing from the, radon measuring equipment unit into the ambient surroundings.

4. The method according to claim 1, wherein the water and the measuring gas are guided parallel to the counter-current along the membrane.

5. The method according to claim 1, wherein the water and the measuring gas are guided parallel to the membrane.

6. The method according to claim 1, wherein the zone is a diffusion hose.

7. A device for continual detection in changes of concentration of radon gas dissolved in water comprising:

a gas source providing a continuous flow of gas;

a gas zone having an inlet and an outlet and being immersed in flowing water a radon measuring equipment unit having an inlet and an outlet;

the gas source providing an continuous flow of gas being connected to the inlet of the gas zone; and the outlet of the gas zone being connected to the inlet of a radon measuring equipment unit from where the flow of gas exits.

8. A device according to claim 7, wherein the outlet of the radon measuring equipment unit opens out in the ambient air.

9. A device according to claim 7, wherein the gas zone is diffusion hose.

* * * * *